United States Patent
Cuccia et al.

(12) 
(10) Patent No.: US 6,281,219 B1
(45) Date of Patent: Aug. 28, 2001

(54) ACARICIDAL AND INSECTICIDAL SUBSTITUTED PYRIMIDINES AND A PROCESS FOR THE PREPARATION THEREOF

(75) Inventors: Salvatore John Cuccia, Lawrence; William Wakefield Wood, Pennington, both of NJ (US); Brian Lee Buckwalter, Yardley; John Francis Chiarello, Newton, both of PA (US); Linda Barbara Fleming, Ewing, NJ (US)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/351,547

(22) Filed: Jul. 12, 1999

Related U.S. Application Data

(60) Provisional application No. 60/092,775, filed on Jul. 14, 1998.

(51) Int. Cl.[7] .......................... A01N 43/54; C07D 239/26; C07D 239/46; C07D 239/60
(52) U.S. Cl. .......................... 514/256; 514/269; 514/272; 514/274; 514/275; 544/299; 544/301; 544/302; 544/303; 544/309; 544/311; 544/312; 544/314; 544/315; 544/316; 544/317; 544/318; 544/319; 544/321; 544/322; 544/323; 544/326; 544/327; 544/329; 544/330; 544/332; 544/335

(58) Field of Search .................................... 544/299, 301, 544/302, 303, 309, 311, 314, 315, 312, 327; 514/256, 274

(56) References Cited

U.S. PATENT DOCUMENTS 5,707,995    1/1998   Munro et al. ........................ 514/256

FOREIGN PATENT DOCUMENTS

| 468695 | 7/1991 | (GB) . |
| WO 98/12184 | 3/1998 | (WO) . |

*Primary Examiner*—John M. Ford
(74) *Attorney, Agent, or Firm*—Barbara V. Maurer

(57) ABSTRACT

The present invention provides compounds of Formula I

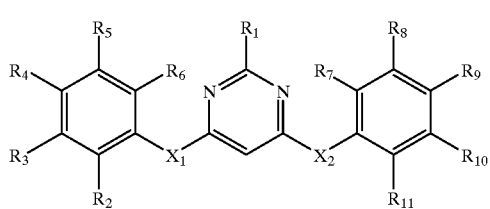

methods for their preparation and their use as acaricidal and insecticidal agents.

16 Claims, No Drawings

ACARICIDAL AND INSECTICIDAL SUBSTITUTED PYRIMIDINES AND A PROCESS FOR THE PREPARATION THEREOF

This application claims benefit of Provisional Application Ser. No. 60/092,775 filed Jul. 14, 1998.

BACKGROUND OF THE INVENTION

A class of pesticidal diaryl pyrimidine compounds is disclosed in U.S. Pat. No. 5,707,995. These compounds all contain 4,6-bis-aryl-pyrimidines wherein the aromatic groups are attached via two linking groups which are identical to one another. The present invention relates to a class of 4,6-bis-aryl-pyrimidines linked by different functional groups which has surprisingly been found to have acaricidal and insecticidal activity.

SUMMARY OF THE INVENTION

The present invention provides compounds of Formula I

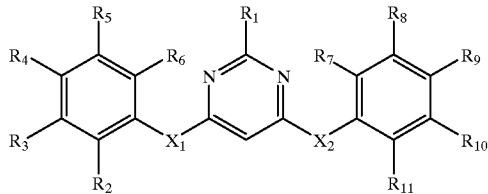

wherein $R_1$ is hydrogen, $(C_{1-6})$alkylthio, halo$(C_{1-6})$alkylthio $(C_{1-6})$alkylsulphinyl, halo$(C_{1-6})$alkylsulphinyl, $(C_{1-6})$alkylsulphonyl, halo$(C_{1-6})$alkylsulphonyl or $NR_{12}R_{13}$;

$R_{12}$ and $R_{13}$ are each independently hydrogen, $(C_{1-6})$alkyl, or halo$(C_{1-6})$alkyl;

$R_2$, $R_3$, $R_4$, $R_5$, $R_6$, $R_7$, $R_8$, $R_9$ and $R_{11}$ are each independently selected from hydrogen, halogen, cyano, nitro, $(C_{1-6})$alkyl, halo$(C_{1-6})$alkyl, $(C_{1-6})$alkoxy, halo $(C_{1-6})$alkoxy, $(C_{1-6})$alkoxy$(C_{1-6})$alkyl, halo$(C_{1-6})$alkoxy$(C_{1-6})$alkyl, $(C_{1-6})$alkylthio, halo$(C_{1-6})$alkylthio, $(C_{1-6})$alkyl sulphinyl, halo$(C_{1-6})$alkylsulphinyl, $(C_{1-6})$alkylsulphonyl, halo$(C_{1-6})$alkylsulphonyl, amino, $(C_{1-6})$alkylamino, di$(C_{1-6})$alkylamino, halo$(C_{1-6})$alkylamino, $(C_{1-6})$alkylhaloalkyl $(C_{1-6})$ amino, dihalo $(C_{1-6})$alkylamino, $(C_{1-6})$alkyloxy-carbonyl, halo$(C_{1-6})$alkyloxycarbonyl, $(C_{2-6})$alkenyl, halo$(C_{2-6})$alkenyl, $(C_{2-6})$alkynyl, halo$(C_{2-6})$alkynyl;

$R_{10}$ is halogen, halo$(C_{1-6})$alkyl, halo$(C_{2-6})$alkenyl or halo $(C_{2-6})$alkynyl;

and $X_1$ and $X_2$ are independently selected from the group consisting of $NR_{14}$, $NR_{15}$, O, $CH_2$, $CR_{18}R_{19}$, CO, C=$NOR_{20}$;

wherein $R_{14}$ is $(C_{1-6})$alkyl;

$R_{15}$ is H, $(C_{1-6})$alkyl or $CH(OR_{16})(OR_{17})$;

$R_{16}$ and $R_{17}$ are each independently $(C_{1-6})$alkyl;

$R_{18}$ and $R_{19}$ each independently selected from H, $(C_{1-6})$alkyl, $(C_{2-6})$alkenyl and $(C_{2-6})$alkynyl which are all optionally substituted by one or more halogens which are the same or different, or $R_{18}$ and $R_{19}$ may together form a carbocyclic ring which is optionally substituted by one or more halogens which are the same or different; $R_{20}$ is $(C_{1-6})$alkyl;

with the proviso that $X_1$ cannot be the same as $X_2$.

Also provided are a process for the preparation of the formula I compound and a method for the control of acarina and insects therewith.

DETAILED DESCRIPTION OF THE INVENTION

Preferred compounds of the present invention include compounds of Formula I

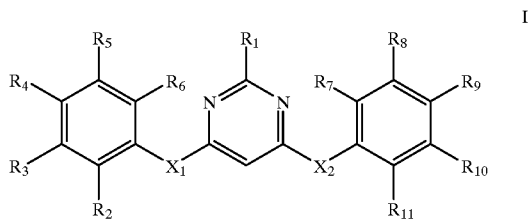

wherein $R_1$ is hydrogen, $(C_{1-6})$alkylthio, halo$(C_{1-6})$alkylthio $(C_{1-6})$alkylsulphinyl, halo$(C_{1-6})$alkylsulphinyl, $(C_{1-6})$alkylsulphonyl, halo$(C_{1-6})$alkylsulphonyl or $NR_{12}R_{13}$;

$R_{12}$ and $R_{13}$ are each independently hydrogen, $(C_{1-6})$alkyl, or halo$(C_{1-6})$alkyl;

$R_2$, $R_3$, $R_4$, $R_5$, $R_6$, $R_7$, $R_8$, $R_9$ and $R_{11}$ are each independently selected from hydrogen, halogen, cyano, nitro, $(C_{1-6})$alkyl, halo$(C_{1-6})$alkyl, $(C_{1-6})$alkoxy, halo $(C_{1-6})$alkoxy, $(C_{1-6})$alkoxy$(C_{1-6})$alkyl, halo$(C_{1-6})$alkoxy$(C_{1-6})$alkyl, $(C_{1-6})$alkylthio, halo$(C_{1-6})$alkylthio, $(C_{1-6})$alkyl sulphinyl, halo$(C_{1-6})$alkylsulphinyl, $(C_{1-6})$alkylsulphonyl, halo$(C_{1-6})$alkylsulphonyl, amino, $(C_{1-6})$alkylamino, di$(C_{1-6})$alkylamino, halo$(C_{1-6})$alkylamino, $(C_{1-6})$alkylhalo$(C_{1-6})$alkylamino, dihalo $(C_{1-6})$alkylamino, $(C_{1-6})$alkyloxycarbonyl, halo$(C_{1-6})$alkyloxycarbonyl, $(C_{2-6})$alkenyl, halo$(C_{2-6})$alkenyl, $(C_{2-6})$alkynyl, halo$(C_{2-6})$alkynyl;

$R_{10}$ is halogen, halo$(C_{1-6})$alkyl, halo$(C_{2-6})$alkenyl or halo $(C_{2-6})$alkynyl;

and a) one of $X_1$ and $X_2$ is $NR_{14}$ and the other is O or S, wherein $R_{14}$ is $(C_{1-6})$alkyl or b) one of $X_1$ and $X_2$ is $NR_{15}$ and the other is $CH_2$, wherein $R_{15}$ is H, $(C_{1-6})$alkyl or $CH(OR_{16})(OR_{17})$ and $R_{16}$ and $R_{17}$ are each independently $(C_{1-6})$alkyl;

or c) one of $X_1$ and $X_2$ is $CR_{18}R_{19}$ or CO and the other is O, wherein $R_{18}$ and $R_{19}$ each independently selected from H, $(C_{1-6})$alkyl, $(C_{2-6})$alkenyl and $(C_{2-6})$alkynyl which are all optionally substituted by one or more halogens which are the same or different, or $R_{18}$ and $R_{19}$ may together form a carbocyclic ring which is optionally substituted by one or more halogens which are the same or different or d) one of $X_1$ and $X_2$ is C=$NOR_{20}$ and the other is $CH_2$, wherein $R_{20}$ is $(C_{1-6})$alkyl with the proviso that the formula I compound is not 4-[m-(trifluoromethyl)benzyl]-6-($\alpha,\alpha,\alpha$-trifluoro-N-methyl-m-toluidino)pyrimidine.

When used herein as a definition or part of a definition the term halogen or halo refers to fluorine, chlorine, bromine and iodine; preferred halogens are fluorine and chlorine; more preferred is fluorine.

When used herein as a definition or part of a definition the term alkyl is a straight or branched chain group such as methyl, ethyl, n-propyl, i-propyl, n-butyl, s-butyl, t-butyl, n-pentyl, 2-pentyl, 3-pentyl and n-hexyl. Preferred alkyl groups are methyl, ethyl, n-propyl, i-propyl, n-butyl, s-butyl, t-butyl and n-pentyl; more preferred alkyl groups are methyl and ethyl.

When used herein as a definition or part of a definition the term alkenyl is a straight or branched chain group such as vinyl, 1-propenyl, 2-propenyl, 1-butenyl, 2-butenyl, 3-butenyl, pentenyls and hexenyls.

When used herein as a definition or part of a definition the term alkynyl is a straight or branched chain group such as ethynyl, 1-propynyl, 2-propynyl, 1-butynyl, 2-butynyl and 3-butynyl.

$R_{10}$ is preferably chlorine, halo($C_{1-4}$)alkyl or halovinyl; more preferably chlorine or a ($C_{1-4}$)alkyl or vinyl group substituted by one or more fluorine or chlorine atoms; most preferably $CF_3$ or $CF_2CF_3$.

$R_3$ is preferably halogen, halo($C_{1-6}$)alkyl, halo($C_{2-6}$)alkenyl or halo($C_{2-6}$)alkynyl; more preferably $R_3$ is halo, halo($C_{1-4}$)alkyl or halovinyl; most preferably chlorine or a ($C_{1-4}$)alkyl or vinyl group substituted by one or more fluorine or chlorine atoms; particular examples of $R_3$ are chlorine, $CF_3$ or $CF_2CF_3$.

$R_4$ and $R_9$ are each preferably selected from hydrogen, halogen, cyano, nitro, ($C_{1-6}$)alkyl, halo($C_{1-6}$)alkyl, ($C_{1-6}$) alkoxy, halo ($C_{1-6}$)alkoxy, ($C_{1-6}$)alkoxy($C_{1-6}$)alkyl, halo($C_{1-6}$)alkoxy($C_{1-6}$)alkyl, ($C_{1-6}$)alkylthio, ($C_{2-6}$)alkenyl, halo($C_{2-6}$)alkenyl, ($C_{2-6}$)alkynyl, halo($C_{2-6}$)alkynyl; more preferably hydrogen or a halogen, most preferably fluorine or chlorine.

$R_2$, $R_5$, $R_6$, $R_7$, $R_8$ and $R_{11}$ are each preferably selected from hydrogen, halogen, cyano, nitro, ($C_{1-6}$)alkyl, halo($C_{1-6}$)alkyl, ($C_{1-6}$)alkoxy, halo ($C_{1-6}$)alkoxy, ($C_{1-6}$)alkoxy($C_{1-6}$)alkyl, halo($C_{1-6}$)alkoxy($C_{1-6}$)alkyl, ($C_{1-6}$)alkylthio, ($C_{2-6}$)alkenyl, halo($C_{2-6}$)alkenyl, ($C_{2-6}$)alkynyl, halo($C_{2-6}$)alkynyl; more preferably each is hydrogen or a halogen, most preferably hydrogen.

$R_{12}$ and $R_{13}$ are each preferably selected from methyl, ethyl, propyl or butyl, more preferably they are both methyl. $R_{14}$, $R_{15}$, $R_{16}$ and $R_{17}$ are each preferably methyl, ethyl, propyl or butyl, more preferably methyl or ethyl. Preferred compounds being those in which $R_{16}$ and $R_{17}$ are identical.

$R_{18}$ and $R_{19}$ are preferably methyl, ethyl, propyl, butyl or together form a cyclopropyl, cyclobutyl or cyclopentyl ring. More preferably both $R_{12}$ and $R_{13}$ are methyl or they together form a cyclopropyl ring.

A preferred group of compounds are those wherein $X_1$ is $NR_{14}$ and $X_2$ is O. Preferred embodiments within this group are those wherein $R_3$, $R_4$ and $R_9$ are independently selected from hydrogen, halo, halo($C_{1-6}$)alkyl, halo($C_{2-6}$)alkenyl or halo($C_{2-6}$)alkynyl. Preferred compounds within this group are those wherein $R_{10}$ is halo($C_{1-6}$)alkyl and $R_9$ is hydrogen or a halogen, particularly compounds wherein $R_{10}$ is $CF_3$ and $R_9$ is hydrogen, chlorine or fluorine. More preferred compounds within this group are those wherein $R_4$ is hydrogen or a halogen and $R_3$ is halo($C_{1-6}$)alkyl, particularly where $R_4$ is hydrogen, chlorine or fluorine and $R_3$ is $CF_3$. Most preferred compounds within this group are those wherein $R_3$ and $R_{10}$ are $CF_3$ and $R_4$ and $R_9$ are fluorine or chlorine, preferably fluorine. Also preferred are compounds wherein $R_3$ and $R_4$ are both halogens, particularly those compounds wherein $R_3$ and $R_4$ are both chlorine. In these embodiments $R_2$, $R_5$, $R_6$, $R_7$, $R_8$ and $R_{11}$ are preferably hydrogen and $R_{14}$ is preferably methyl or ethyl, more preferably methyl.

Preferred compounds within this group are:

4-[(α,α,α,4-Tetrafluoro-N-methyl-m-toluidino)-6[(α,α,α,4-tetrafluoro-m-tolyl)oxy]pyrimidine;
4-(α,α,α,-Trifluoro-N-methyl-m-toluidino)-6-[(α,α,α-trifluoro-m-tolyl)oxy]pyrimidine;
4-[(α,α,α,4-Tetrafluoro-n-methyl-m-toluidino)-6-[(α,α,α,4-tetrafluoro-m-tolyl)oxy}pyrimidine;
4-(3,4-Dichlorophenoxy)-6-(α,α,αtrifluoro-N-methyl-m-toluidino)pyrimidine;
4-[(4-Chloro-α,α,α-trifluoro-m-tolyl)oxy]-6-(α,α,α-trifluoro-N-methyl-m-toluidino)pyrimidine;
4-(α,α,α,4-Tetrafluoro-N-methyl-m-toluidino)-6-[(α,α,α-trifluoro-m-tolyl)oxy]pyrimidine;
4-[(4-Chloro-α,α,α,-trifluoro-m-tolyl)oxy]-6-(α,α,α,4-tetrafluoro-N-methyl-m-toluidino)pyrimidine;
4-(4-Chloro-α,α,α,-trifluoro-N-methyl-m-toluidino)-6-[(α,α,α,4-tetrafluoro-m-tolyl)oxy]pyrimidine;
4-(3,4-Dichloro-N-methylanilino)-6-[(α,α,α,-trifluoro-m-tolyl)oxy]pyrimidine;
4-(3,4-Dichloro-N-methylanilino)-6-[(α,α,α,-4-tetrafluoro-m-tolyl)oxy]pyrimidine; and
4-(3,4-Dichloro-N-methylanilino)-6-(3,4-dichlorophenoxy)pyrimidine.

A further preferred group of compounds are those wherein $X_1$ is $CH_2$ and $X_2$ is $NR_{15}$. Preferred embodiments within this group are those wherein $R_3$, $R_4$ and $R_9$ are independently selected from hydrogen, halo, halo($C_{1-6}$)alkyl, halo ($C_{2-6}$)alkenyl or halo($C_{2-6}$)alkynyl. Preferred compounds within this group are those wherein $R_{10}$ is halo($C_{1-6}$)alkyl and $R_9$ is hydrogen or a halogen, particularly compounds wherein $R_{10}$ is $CF_3$ and $R_9$ is hydrogen, chlorine or fluorine. More preferred compounds within this group are those wherein $R_3$ is halo($C_{1-6}$)alkyl and $R_4$ is hydrogen or a halogen, particularly where $R_3$ is $CF_3$ and $R_4$ is hydrogen, chlorine or fluorine. Most preferred compounds within this group are those wherein $R_3$ and $R_{10}$ are $CF_3$ and $R_4$ and $R_9$ are fluorine or chlorine, preferably fluorine. Also preferred are compounds wherein $R_3$ and $R_4$ are both halogens, particularly those compounds wherein $R_3$ and $R_4$ are both chlorine. In these embodiments $R_2$, $R_5$, $R_6$, $R_7$, $R_8$ and $R_{11}$ are preferably hydrogen and $R_{15}$ is preferably hydrogen, methyl or ethyl, more preferably methyl.

Preferred compounds within this group are:

4-(α,α,α,4-Tetrafluoro-m-toluidino)-6-[m-(trifluoromethyl)benzyl]pyrimidine hydrochloride;
4-(3,4-Dichlorobenzyl)-6-(α,α,α,4-tetrafluoro-m-toluidino)pyrimidine hydrochloride;
4-(4-Chloro-α,α,α,-trifluoro-m-toluidino)-6-[m-(trifluoromethyl)benzyl]pyrimidine hydrochloride;
4-[m-(Trifluoromethyl)benzyl]-6-(α,α,α,-trifluoro-m-toluidino)pyrimidine hydrochloride;
4-(α,α,α,4-Tetrafluoro-N-methyl-m-toluidino)-6-[m-trifluoromethyl)benzyl]pyrimidine;
4-(4-Chloro-α,α,α,-trifluoro-N-methyl-m-toluidino)-6-(3,4-dichlorobenzyl)pyrimidine;
4-(3,4-Dichlorobenzyl)-6-(α,α,α,4-tetrafluoro-N-methyl-m-toluidino)pyrimidine;
4-(4-Chloro-α,α,α,-trifluoro-m-toluidino)-6-(3,4-dichlorbenzyl)pyrimidine;
4-(3,4-Dichlorobenzyl)-6-[N-diethoxymethyl)-α,α,α,4-tetrafluoro-m-toluidino]pyrimidine;
4-(4-Chloro-α,α,α,-trifluoro-N-methyl-m-toluidino)-6-[m-(trifluoromethyl)benzyl]pyrimidine;
4-(3,4-Dichlorobenzyl)-6-(α,α,α,-trifluoro-m-toluidino)pyrimidine;
6-(α,α,α,4-Tetrafluoro-m-toluidino)-4-[4-fluoro-3-(trifluoromethyl)benzyl]pyrimidine;
4-[4-Fluoro-3-(trifluoromethyl)benzyl]-6-(α,α,α,4-tetrafluoro-N-methyl-m-toluidino)pyrimidine;
4-(4-chloro-α,α,α,-trifluoro-m-toluidino)-6-[4-fluoro-3-(trifluoromethyl)benzyl]pyrimidine; and 4-(4-chloro-α,α,α,-trifluoro-N-methyl-m-toluidino)-6-[4-fluoro-3-(trifluoromethyl)benzyl]pyrimidine.

A further preferred group of compounds are those wherein $X_1$ is $CR_{18}R_{19}$ or CO and $X_2$ is O. Preferred embodiments within this group are those wherein $R_3$, $R_4$ and $R_9$ are independently selected from hydrogen, halogen, halo($C_{1-6}$)alkyl, halo($C_{2-6}$)alkenyl or halo($C_{2-6}$)alkynyl. Preferred compounds within this group are those wherein $R_{10}$ is halo($C_{1-6}$)alkyl and $R_9$ is hydrogen or a halogen, particularly where $R_{10}$ is $CF_3$ and $R_9$ is hydrogen, chlorine or fluorine. More preferred compounds within this group are those wherein $R_3$ is hydrogen and $R_4$ is a halogen or wherein $R_3$ is halo($C_{1-6}$)alkyl and $R_4$ is hydrogen, particularly compounds wherein $R_3$ is H or CF3 and $R_4$ is chlorine or hydrogen. Most preferred compounds within this group are those wherein $R_3$ is $CF_3$, $R_4$ and $R_{10}$ are hydrogen and $R_9$ is a halogen, particularly chlorine. In these embodiments $R_2$, $R_5$, $R_6$, $R_7$, $R_8$ and $R_{11}$ are preferably hydrogen and $R_{18}$ and $R_{19}$ are preferably hydrogen, methyl, ethyl or together form a cyclopropyl ring. More preferably $R_{18}$ and $R_9$ are both methyl.

Preferred compounds within this group are:

4-[m-(Trifluoromethyl)benzyl]-6-[(α,α,α,-trifluoro-m-tolyl)oxy]pyrimidine;
4-(p-Chloro-α,α,-dimethylbenzyl)-6-[(α,α,α,4-tetrafluoro-m-tolyl)oxy]pyrimidine;
4-(p-Chloro-α,α,-dimethylbenzyl)-6-[(α,α,α,4-trifluoro-m-tolyl)oxy]pyrimidine;
4-[1-(p-Chlorophenyl)cyclopropyl]-6-[(α,α,α,-trifluoro-m-tolyl)oxy]pyrimidine;
4-[1-(p-Chlorophenyl)cyclopropyl]-6-[(α,α,α,4-tetrafluoro-m-tolyl)oxy]pyrimidine;
6-[(α,α,α,4-Tetrafluoro-m-tolyl)oxy]-4-pyrimidinyl α,α,α,4-trifluoro-m-tolyl ketone;
4-[α,α,-Dimethyl-m-(trifluoro-methyl)benzyl]-6-[α,α,α,-trifluoro-m-tolyl)oxy]pyrimidine; and
4-[α,α,-Dimethyl-m-(trifluoro-methyl)benzyl]-6-[(α,α,α,4-tetrafluoro-m-tolyl)oxy]pyrimidine.

A further preferred group of compounds are those wherein $X_1$ is C=NOR$_{20}$ and $X_2$ is $CH_2$. Preferred embodiments within this group are those wherein $R_3$, $R_4$ and $R_9$ are independently selected from halo($C_{1-6}$)alkyl, halo($C_{2-6}$)alkenyl or halo($C_{2-6}$)alkynyl. Preferred embodiments of the invention within this group are compounds wherein $R_3$ and $R_{10}$ are each hydrogen and at least one of $R_3$ and $R_{10}$ is halo($C_{1-6}$)alkyl. More preferred compounds are those wherein $R_4$ and $R_9$ are both halo($C_{1-6}$)alkyl, particularly compounds wherein $R_3$ and $R_{10}$ are both $CF_3$. In these embodiments $R_2$, $R_5$, $R_6$, $R_7$, $R_8$ and $R_{11}$ are preferably hydrogen and $R_{20}$ is preferably methyl.

A preferred compound within this group is 6-[m-(trifluoromethyl)benzyl]-4-pyrimidinylα,α,α-trifluoro-m-tolyl-ketone, O-methyloxime, (E)— and (Z)—.

A further preferred group of compounds are those compounds wherein one of $X_1$ and $X_2$ is $NR_{14}$ and the other is S or those wherein $R_1$ is ($C_{1-6}$,)alkylthio, halo($C_{1-6}$)alkylthio, ($C_{1-6}$)alkylsulfinyl, halo($C_{1-6}$)alkylsulfinyl, ($C_{1-6}$)alkylsulfoxyl, halo($C_{1-6}$)alkyl-sulfoxyl or $NR_{12}R_{13}$; and one of $X_1$ and $X_2$ is $NR_{14}$ and the other is O.

The compounds of the invention are particularly useful as acaricides or insecticides. They are especially useful for the control of herbivorous mites, including but not limited to, Tetranychidae such as *Tetranychus urticae, Tetranychus pacificus, Tetranychus kanzawai, Panonychus ulmi, Panonychus citri* and *oligonychus pratensis;* Tarsonemidae such as *Phytonemus pallidus* and *Polyphagotarsonemus latus;* Eriophyidae such as *Aculus schlechtendali, Phyllocoptrata ole-ivora* and *Eriophyes sheldoni;* and Tenuipalpidae such as *Brevipalpus phoenicis*. In particular, the compounds of this invention are especially useful for the control of *Tetranychus urticae, Panonychus ulmi, Panonychus citri* and *Brevipalpus phoenicis.*

Plants which are protected from mite infestations by compounds of the present invention include, but are not limited to, citrus plants such as orange, grapefruit, lemon and lime; pome fruits such as apple, pear and kiwi; stone fruits such as avocado, peach, cherry, fig, olive and mango; vine fruits such as grape, strawberry and raspberry; nut crops such as almond, pecan, walnut, pistachio, cashew, filbert, chestnut, macadamia and brazil nut; field crops such as cotton, corn, soybean, wheat, squash and watermelon, ornamental plants such as flowering plants and shrubs; coffee and tea. The compounds of this invention are especially useful for protecting citrus plants and pome fruits from mite infestations.

To provide control of mites, orchard and ornamental plants are generally treated with a liquid, preferably aqueous, dispersion which contains about 1 g/hl to 100 g/hl, preferably 5 g/hl to 20 g/hl of a formula I compounds. In practice the dispersion is generally applied to the orchard or ornamental plant to runoff.

The compounds of this invention are also useful for control of mites in field crops when applied to the crops in sufficient amount to provide a rate of about 50–400 g/ha of active ingredient, more preferably a rate of about 75–250 g/ha of active ingredient.

The term 'foliage' as used herein includes, but is not limited to, the leaves, buds, fruits, stems, twigs, branches and/or flowers of plants. The term 'orchard plant' as used herein includes, but is not limited to, citrus plants, pome fruits, stone fruits, vine fruits and nut crops. The term 'ornamental plant' as used herein includes, but is not limited to flowering plants and shrubs. The term 'field crop' as used herein includes, but is not limited to, vegetables such as squash and watermelon and row crops such as cotton, corn, soybean and wheat.

The invention also relates to compositions comprising a compound of formula I and an agriculturally acceptable carrier. For example, the compounds of this invention may be formulated as emulsifiable concentrates, flowable concentrates or wettable powders which are diluted with water or other suitable polar solvent, generally in situ, and then applied as a dilute spray. They may also be formulated in water dispersible granules, dry compacted granules, granular formulations, dusts, dust concentrates, suspension concentrates, microemulsions and the like. Such formulations or compositions of the present invention include a compound of this invention (or combinations thereof) admixed with one or more agronomically acceptable inert, solid or liquid carriers.

Compounds of the invention wherein $X_1$ is $NR_{14}$ and $X_2$ is O may suitably be prepared by reacting a compound of formula II, wherein $R_1$ is as defined above and the groups Y are the same or different halogens,

II

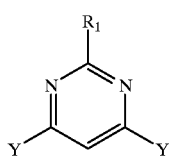

with a compound of formula III

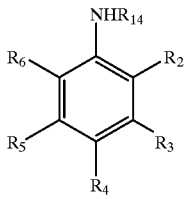
III to provide a compound of formula IV

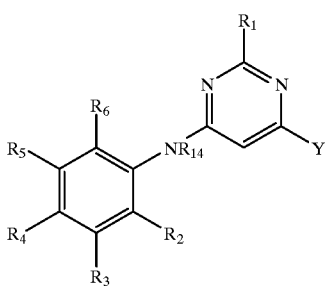
IV and then reacting the compound of formula IV with a phenol of formula V or a thiophenol of formula $V^1$

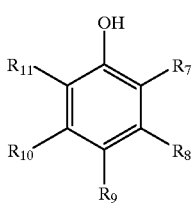
V

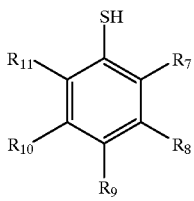
$V^1$ to provide the desired compound of formula I.

Compounds of the invention wherein $X_1$ is O and $X_2$ is $NR_{14}$ may be prepared analogously using the starting materials $III^a$ and $V^a$.

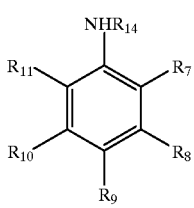
$III^a$

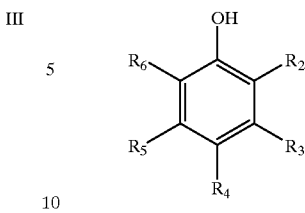
$V^a$

Compounds of the invention wherein $X_1$ is S and $X_2$ is $NR_{14}$ may be prepared analogously using the starting materials $III^a$ and $V^{1a}$

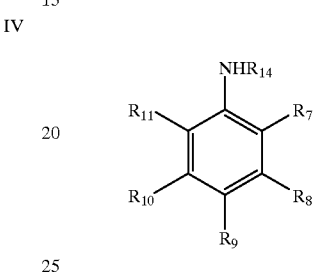
$III^a$

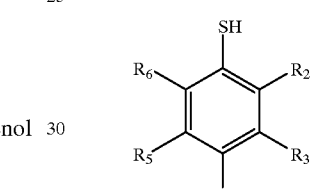
$V^{1a}$

Preparation of compounds of the invention wherein $X_1$ is $CH_2$ and $X_2$ is $NR_{15}$ may suitably be prepared by:

a) halogenating an acid of formula VI

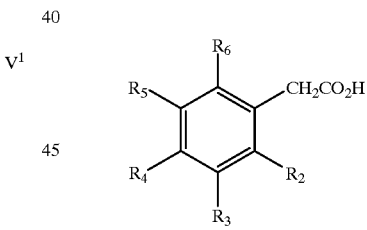
VI to provide an acid halide of formula VII

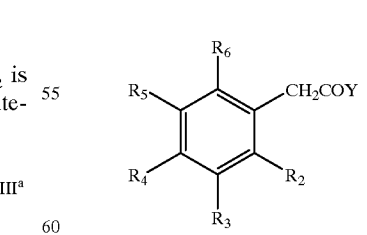
VII wherein Y is a halogen, e.g. by chlorination, in which case Y is chlorine;

b) alkylating the acid halide of formula VII to provide a compound of formula VIII wherein $R_{18}$ is an alkyl group e.g. ethyl

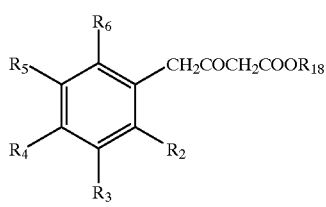

VIII

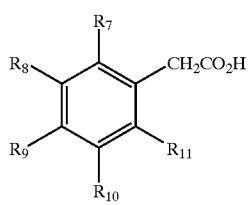

VI$^a$ c) converting the compound of formula VIII to provide a compound of formula IX

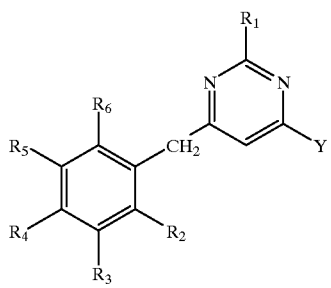

IX

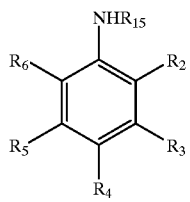

XI$^a$ e.g. by first reacting the compound of formula VIII with ammonium acetate in ethanol and then with formamide and potassium tertiary butoxide;

d) halogenating the compound of formula IX to provide a compound of formula X wherein Y is a halogen

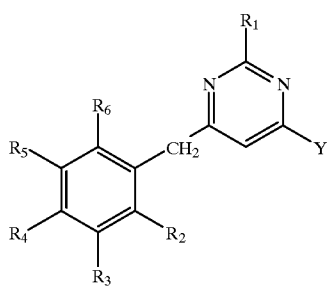

X

Preparation of compounds of the invention wherein $X_1$ is $CH_2$, $X_2$ is O and $R_1$ is hydrogen may suitably be prepared by:

a) reacting a compound of formula XII

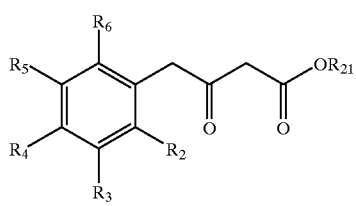

XII wherein $R_{21}$ is an alkyl group; with a compound of formula XIII

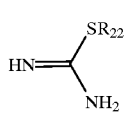

XIII e.g. by chlorination in which case Y is chlorine; and e) converting the compound of formula X to the desired compound of formula I by reacting it with the appropriate aniline derivative of formula XI wherein $R_{22}$ is an alkyl group, to provide a compound of formula XIV,

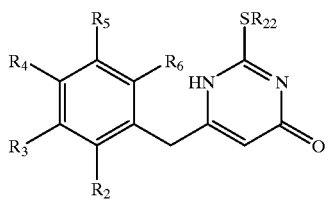

XIV

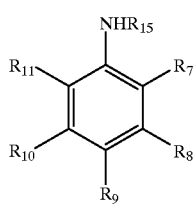

XI

Compounds of formula I wherein $X_1$ is $NR_{15}$ and $X_2$ is $CH_2$ may be prepared analogously using the starting materials VI$^a$ and XI$^a$ preferably in the presence of a base;

b) halogenating the compound of formula XIV to a compound of formula XV:

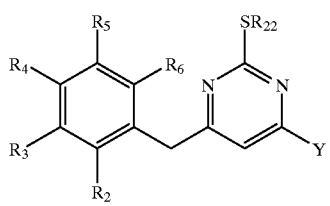

XV wherein Y is a halogen e.g. chlorine, this may suitable be performed by chlorinating the compound of formula XIV, e.g. using phosphorous oxychloride;

c) reacting the compound of formula XV with a phenol of formula V, as described above, to provide a compound of formula XVII:

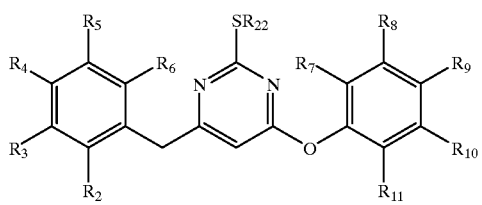

XVII d) oxidising the compound of formula XVII to a compound of formula XVIII:

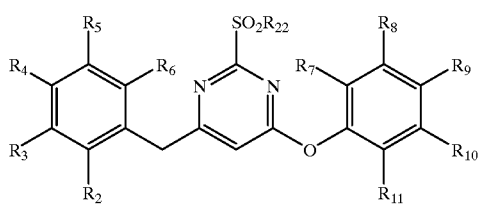

XVIII using a suitable oxidising agent, e.g. m-chlorobenzoic acid;

and e) reducing the compound of formula XVIII using a suitable reducing agent, e.g. sodium borohydride, to provide the desired compound of formula I.

Compounds of the invention wherein $X_2$ is $CR_{18}R_{19}$, $R_{18}$ and $R_{19}$ are both hydrogen, $X_1$ is O and $R_1$ is hydrogen may be prepared analogously using the starting materials $XII^a$

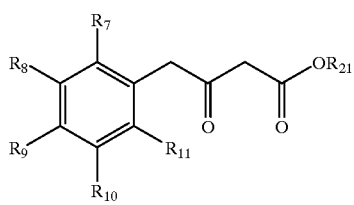

$XII^a$ and $V^a$ described above.

Compounds of the invention wherein $X_1$ is $CH_2$, $X_2$ is O, $R_1$ is $NR_{12}R_{13}$ and $R_{12}$ and $R_{13}$ are as defined above may be prepared by reacting the compound of formula XVIII, with an amine of formula XIX:

NHR$_{12}$R$_{13}$   XIX e.g. using diethylamine to introduce a diethyl amino group.

Similarly, compounds of the invention wherein $X_2$ is $CH_2$, $X_1$ is O, $R_1$ is $NR_{12}R_{13}$, and $R_{12}$ and $R_{13}$ are as defined above, may be prepared analogously by reacting the compound of formula $XVIII^a$

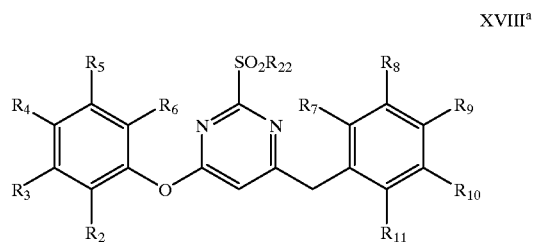

$XVIII^a$ with an amine of formula XIX.

Compounds of the invention wherein $X_1$ is $CR_{18}R_{19}$, $X_2$ is O and $R_{18}$ and $R_{19}$ are the same and are selected from $(C_{1-6})$alkyl, $(C_{2-6})$alkenyl and $(C_{2-6})$alkynyl which are all optionally substituted by one or more halogens which are the same or different may be prepared by:

a) reacting a compound of formula XX

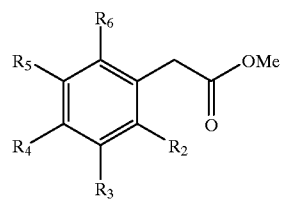

XX with at least 2 equivalents of an iodide of formula XXI, $R_{18}I$, preferably in the presence of a base, to provide a compound of formula XXII

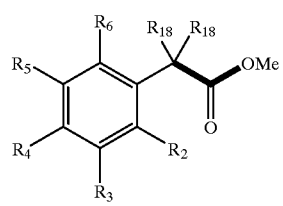

XXII b) saponifying the compound of formula XXII to provide a compound of formula XXIII

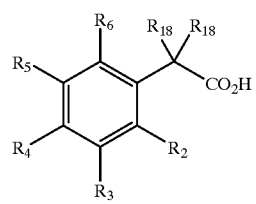

XXIII c) converting the compound of formula XXIII to a compound of formula XXIV

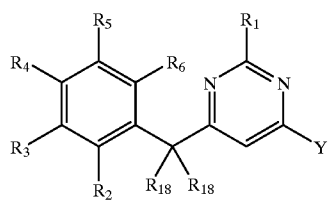

XXIV wherein Y is a halogen, and d) reacting the compound of formula XXIV with a phenol of formula V, as described above, to provide the desired compound of the invention.

Compounds of the invention wherein $X_1$ is O, $X_2$ is $CR_{18}R_{19}$, and $R_{18}$ and $R_{19}$ are the same and are selected from $(C_{1-6})$alkyl, $(C_{2-6})$alkenyl and $(C_{2-6})$alkynyl which are all optionally substituted by one or more halogens which are the same or different may be prepared analogously.

Compounds wherein $R_{18}$ and $R_{19}$ are identical may be prepared using at least 2 equivalents of the same iodide whereas compounds wherein $R_{18}$ and $R_{19}$ are different to one another may be prepared by the sequential use of no greater than one equivalent of each of two different alkyl halides. Spiro compounds may be prepared from appropriate alkyldihalides.

Compounds of the invention wherein $X_1$ is CO and $X_2$ is O may be prepared from the corresponding compound wherein $X_1$ is $CH_2$, e.g. by air oxidation. Similarly compounds of the invention wherein $X_1$ is O and $X_2$ is CO may suitably be prepared by converting the corresponding compound wherein $X_2$ is $CH_2$.

Compounds of the invention wherein $X_1$ is $C=NOR_{20}$ and $X_2$ is $CH_2$ may be prepared by:

a) converting the compound of formula $X^a$

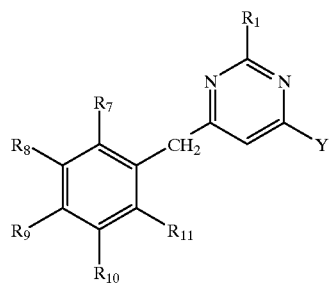

$X^a$ to a compound of formula XXVIII

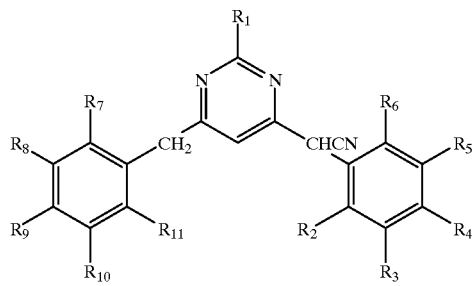

XXVIII b) treating the compound of formula XXVIII with aqueous base to provide a compound of formula XXIX

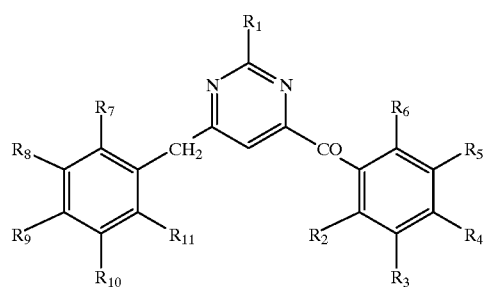

XXIX and c) converting the compound of formula XXIX into the corresponding oxime.

Compounds of the invention wherein $X_2$ is $C=NOR_{20}$ and $X_1$ is $CH_2$ may be similarly prepared by using compounds of formula X and $V^a$, as described above, as starting materials.

Accordingly, the present invention also provides a process for the preparation of a compound of formula I which comprises the following steps:

i) reacting a compound of formula IV

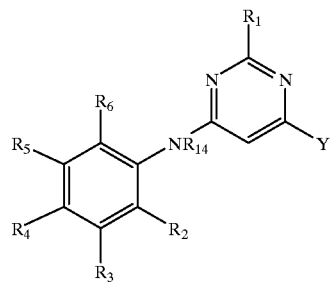

IV with a phenol of formula V

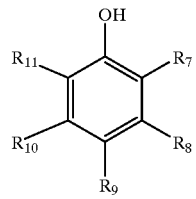

V to provide a compound of formula I wherein $X_1$ is $NR_{14}$ and $X_2$ is O;

ii) reacting a compound of formula $IV^a$

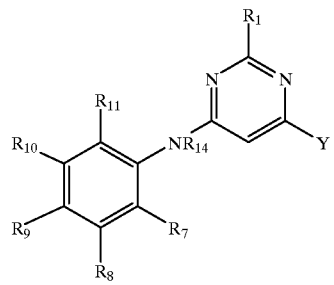

$IV^a$ with a phenol of formula V$^a$

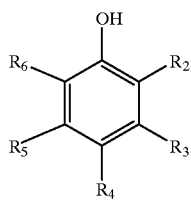

V$^a$ to provide a compound of formula I wherein $X_1$ is O and $X_2$ is $NR_{14}$;

iii) reacting a compound of formula X

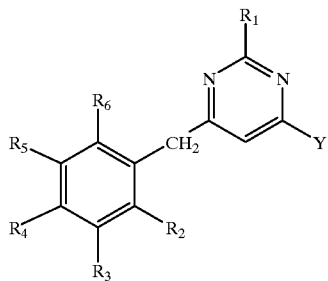

X wherein Y is a halogen, with the appropriate aniline derivative of formula XI

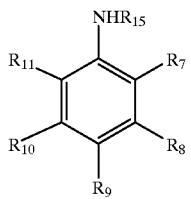

XI to provide a compound of formula I wherein $X_1$ is $CH_2$ and $X_2$ is $NR_{15}$;

iv) reacting a compound of formula X$^a$

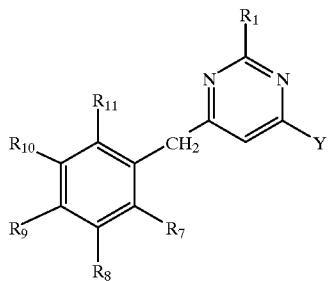

X$^a$ wherein Y is a halogen, with the appropriate aniline derivative of formula XI$^a$

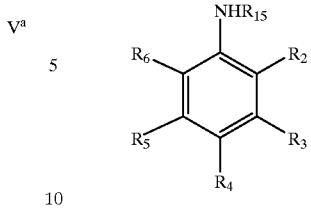

XI$^a$ to provide a compound of formula I wherein $X_1$ is $NR_{15}$ and $X_2$ is $CH_2$;

v) reducing a compound of formula XVIII

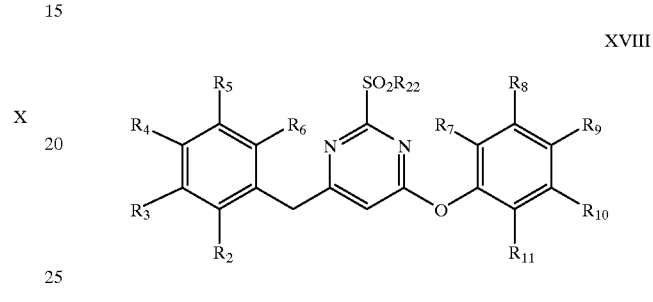

XVIII to provide a compound of formula I wherein $X_1$ is $CH_2$, $X_2$ is O and $R_1$ is hydrogen;

vi) reducing a compound of formula XVIII$^a$

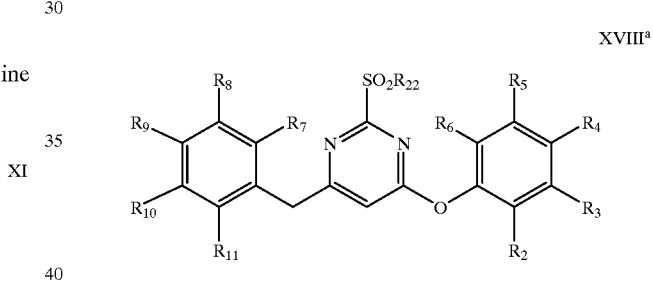

XVIII$^a$ to provide a compound of formula I wherein $X_1$ is O, $CH_2$, X is O and $R_1$ is hydrogen;

vii) reacting a compound of formula XVIII with an amine of formula XIX:

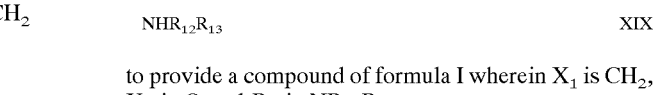

$NHR_{12}R_{13}$    XIX to provide a compound of formula I wherein $X_1$ is $CH_2$, $X_2$ is O and $R_1$ is $NR_{12}R_{13}$;

viii) reacting a compound of formula XVIII$^a$ with an amine of formula XIX, as described above, to provide a compound of formula I wherein $X_1$ is O, $X_2$ is $CH_2$ and $R_1$ is $NR_{12}R_{13}$;

ix) reacting a compound of formula XXIV

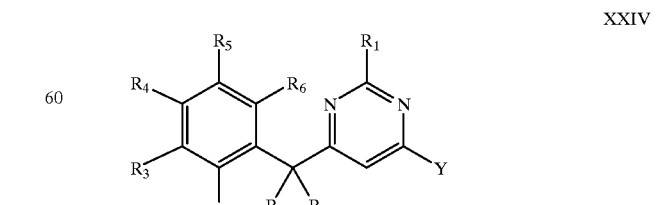

XXIV with a phenol of formula XVI

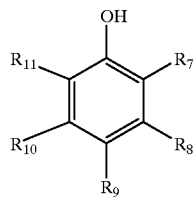

to provide a compound of formula I wherein $X_1$ is $CR_{18}R_9$, $X_2$ is O and $R_{18}$ and $R_{19}$ are each selected from $(C_{1-6})$alkyl, $(C_{2-6})$alkenyl and $(C_{2-6})$alkynyl which are all optionally substituted by one or more halogens which are the same or different, or $R_{18}$ and $R_{19}$ may together form a carbocyclic ring which is optionally substituted by one or more halogens which are the same or different;

x) reacting a compound of formula XXIV$^a$

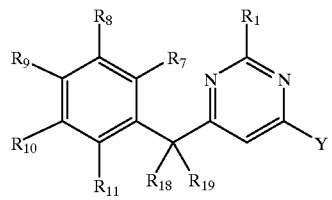

wherein Y is a halogen, with a phenol of formula V$^a$

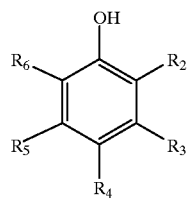

to provide a compound of formula I wherein $X_1$ is O and $X_2$ is $CR_{18}R_{19}$, wherein $R_{18}$ and $R_{19}$ are each selected from $(C_{1-6})$alkyl, $(C_{2-6})$alkenyl and $(C_{2-6})$alkynyl which are all optionally substituted by one or more halogens which are the same or different, or $R_{18}$ and $R_{19}$ may together form a carbocyclic ring which is optionally substituted by one or more halogens which are the same or different;

xi) converting a compound of formula I wherein $X_1$ is $CR_{18}R_{19}$ and $X_2$ is O to the corresponding compound wherein $X_1$ is CO;

xii) converting a compound of formula I wherein $X_2$ is $CR_{18}R_{19}$ and $X_1$ is O to the corresponding compound wherein $X_2$ is CO;

xiii) converting a compound of formula XXIX

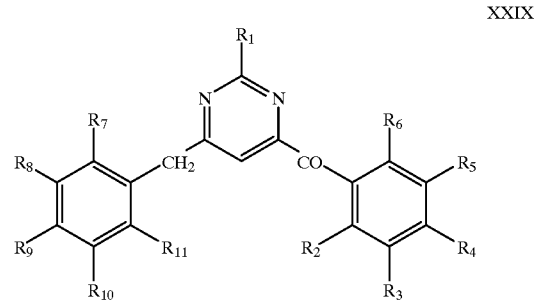

into the corresponding oxime to provide a compound of formula I wherein $X_1$ is $C=NOR_{20}$ and $X_2$ is $CH_2$;

and xiv) converting a compound of formula XXIX$^a$

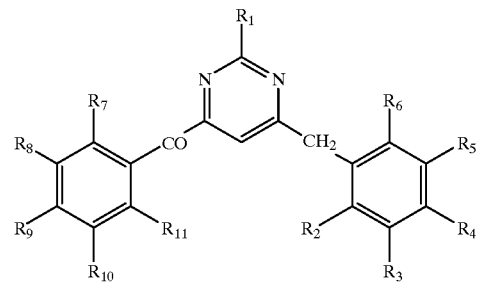

into the corresponding oxime to provide a compound of formula I wherein $X_1$ is $CH_2$ and $X_2$ is $C=NOR_{20}$.

For a more clear understanding of the present invention, the following examples are presented by way of illustration only. The invention is not to be deemed limited thereby.

EXAMPLE 1

Preparation of Pyrimidine, 4-(a, α,α,4-tetrafluoro-m-toluidino)-6-[m-(trifluoromethyl)benzyl] hydrochloride (3-Trifluoromethylphenyl)acetic acid (25.1 g, 0.12 mol) is added to a solution of dichloromethane (200 ml) and dimethylformamide (1 ml). Thionyl chloride (18.2 g, 0.15 mol) is then added dropwise and the resulting solution is stirred overnight. The solution is then concentrated under reduced pressure to give the crude acid chloride in nearly quantitative yield. The potassium salt of ethyl malonate (41.3 g, 0.24 mmol) is dissolved in acetonitrile (400 ml) and is cooled to 0° C. Triethylamine (23.23 g, 0.23 mol) and magnesium chloride(28.8 g, 0.30 mol) are then added and the slurry is warmed to 25° C. and is stirred for 2 hours. The slurry then is cooled to 0° C. and the acid chloride is added over 1 hour. The mixture is allowed to warm to room temperature and is stirred overnight. The solvent is removed under reduced pressure and the resulting solid is suspended in toluene (200 ml) and is cooled to 0° C. Ice cold 4N hydrochloric acid is then slowly added. The organic phase is separated and washed with 4N hydrochloric acid, water and finally saturated brine. The organic phase is dried and concentrated. The crude product is then purified by distillation to give ethyl-(3-trifluoromethylphenyl) acetoacetate (15.4 g).

Ethyl-(3-trifluoromethylphenyl)acetoacetate (15.3 g, 0.056 mol) is added to a solution of ammonium acetate (21.6 g, 0.28 mol) in ethanol (100 ml) and the mixture is refluxed for 3 hours. The solution is concentrated under reduced pressure and then suspended in ethyl acetate. The suspension is washed with water and saturated brine and the organic layer concentrated. The material is then dissolved in dimethylsulfoxide (125 ml) and formamide (20 ml) and potassium tert-butoxide (1.28 g, 0.011 mol) are added. The solution is heated for 18 hours at 100° C. Upon cooling the solution is poured into ice (1000 ml) and glacial acetic acid (20 ml). The resulting solid is collected and air dried. The material is then triturated with diethyl ether and is air dried to give 6-(3-trifluoromethylbenzyl)pyrimidin-4-one (7.20 g).

Under nitrogen atmosphere, 6-(3-trifluoromethylbenzyl)pyrimidin-4-one (7.0 g, 0.027 mol) is dissolved in phosphorus oxychloride (30 ml) and is refluxed for 1.5 hours. After cooling the solution is concentrated under reduced pressure. The solid is then dissolved in ethyl acetate, washed with water, saturated brine, dried and the crude product purified by flash column chromatography to give 6-(3-trifluoromethylbenzyl)-4-chloro-pyrimidine (6.3 g).

6-(3-Trifluoromethylbenzyl)-4-chloro-pyrimidine (1.5 g, 0.0055 mol) and 3-trifluoromethyl-4-fluoroaniline (0.92 g, 0.0055 mol) is heated together in the absence of solvent at 100° C. for 1 h. The resulting solid is washed with diethyl ether and air dried to give 4-($\alpha,\alpha,\alpha$,4-tetrafluoro-m-toluidino)-6-[m-(trifluoromethyl)benzyl]pyrimidine hydrochloride (2.2 g).

EXAMPLES 2–16

Preparation of Substituted Pyrimidine Compounds

Using essentially the same procedure described hereinabove for Example 1 and employing the appropriate starting materials and reagents, the following compounds wherein $X_1$ is $CH_2$ and $X_2$ is $NR15$ and $R_1$, $R_2$, $R_5$, $R_6$, $R_7$, $R_8$ and $R_{11}$ are prepared.

| Example | $R_4$ | $R_3$ | $R_9$ | $R_{10}$ | $R_{15}$ | M.p (C) |
|---|---|---|---|---|---|---|
| 2 | Cl | Cl | F | $CF_3$ | H | 222–225 |
| 3 | H | $CF_3$ | Cl | $CF_3$ | H | 238–241 |
| 4 | H | $CF_3$ | Cl | $CF_3$ | H | 228–231 |
| 5 | Cl | $CF_3$ | F | $CF_3$ | Me | 96.5–98.5 |
| 6 | Cl | Cl | Cl | $CF_3$ | Me | 72–75 |
| 7 | Cl | Cl | F | $CF_3$ | Me | 60–63 |
| 8 | Cl | Cl | Cl | $CF_3$ | H | 93–95 |
| 9 | Cl | Cl | F | $CF_3$ | CH(OEt)2 | oil |
| 10 | H | H | Cl | $CF_3$ | Me | 92–94 |
| 11 | Cl | Cl | H | $CF_3$ | H | 111–113 |
| 12 | Cl | Cl | H | $CF_3$ | Me | 62–64 |
| 13 | F | F | F | $CF_3$ | H | 45–47 |
| 14 | F | F | F | $CF_3$ | Me | 104–107 |
| 15 | F | F | Cl | $CF_3$ | H | 45–50 |
| 16 | F | F | Cl | $CF_3$ | Me | 91–94 |

EXAMPLE 17

Insecticide and Acaricidal Evaluation of Test Compounds

The activity of the compounds prepared is determined by preparing stock solutions of test samples at 4000 ppm in acetone/water and diluted appropriately for the following assays:

Southern Army Worm (*Spodoptera eridania*, SAW)

Excised lima bean leaves are dipped into the test solution and held upright for 10 minutes to allow complete evaporation of the solvent. Four leaves are placed in a test cup (8 oz, paper) and 3 sheets of filter paper added. Each cup is treated with 5 second instar *S. eridania* larvae and the cup capped. Test cups are maintained at 27°–28° C. and 50% humidity for 5 days. Mortality is then observed and rated according to the scale below.

Twospotted Spider Mite (*Tetranychus urticae*, TSM)

Lima bean plants grown to the primary leaf stage with leaves approximately 7 cm in length are infested with mites by placing a heavily infested leaf on each leaf of the test plant. Mites are allowed to transfer for at least two hours. The infested leaves of the intact plant are dipped into the test solution to provide complete coverage of the leaf surfaces. Plants are maintained under GRO-LUX lights (24-hour photoperiod) at 27–28° C. for 5 days. Mortality is observed of treat mites and surviving population and rated according to the scale below.

Western Corn Rootworm (*Diabrotica virgifera virgifera*, WCR)

Millet seeds (Panicum spp.) are soaked in water one day prior to testing to initiate seed germination Test solutions are added to 4 fl.oz. specimen cups and the acetone is allowed to evaporate. Dry soil (30 g/cup) is added to each cup and the water/test material solution 1 is allowed to disperse through the soil for a minimum of hour. Presoaked millet seed (1 cc.) is added to each cup and the cup is shaken vigorously to incorporate the test material and seed evenly throughout the soil. Each cup is then infested with 10 second instar WCR larvae and re-capped. Five small holes are inserted in each cup lid for ventilation. Test cups are maintained at 27–28° C. and 50% humidity for 5 days. Mortality is then observed and rated according to the scale below.

Insecticide Diet Assay (Miniscreen)

Targets: Southern Armyworm (*Spodoptera eridania*, SAW) and Southern Corn Rootworm (*Diabrotica undecimpunctata howardi*, SCR).

Insect diet (Southland for SAW, and Bioserve #9800 for SCR) is poured into 128 well bioassay trays. Test compounds, rendered in 96-well deepwell microtiter plates, are reconstituted to the appropriate test concentration (3000 ppm for SAW and 1000 ppm for SCR) using 100% acetone as the solvent. A total of four diet wells (two reps for each species) are each treated with 50 ml of test solution. The acetone is allowed to evaporate leaving the dried compound covering the surface of the diet well. Eggs of each test target are suspended in a 0.2% agar solution at a density of 10–20 eggs per 20 ml. A total of 20 ml of each egg suspension is pipetted onto the surface of each treated well on the appropriate diet. The agar is allowed to dry off leaving the eggs sitting on the surface of the contaminated diet. The trays are covered with vented, resealable lids and incubated at 25° C. for seven days. Mortality is then observed according to the scale below.

The results are rated according to the following table:

| |
|---|
| 0 = no effect |
| 1 = 10–25% |
| 2 = 26–35% |
| 3 = 36–45% |
| 4 = 46–55% |
| 5 = 56–65% |
| 6 = 66–75% |
| 7 = 76–85% |
| 8 = 86–99% |
| 9 = 100% |

The results are shown in the following table:

| | TSM twospotted mite | | | SAW southern army worm | | | | |
|---|---|---|---|---|---|---|---|---|
| Example | 300 (ppm) | 100 (ppm) | 10 (ppm) | 3000 (ppm) | 1000 (ppm) | 300 (ppm) | 100 (ppm) | 10 (ppm) |
| 1 | 9 | 8 | 0 | | | 9 | 7 | 0 |
| 2 | 8 | 0 | 0 | | 0 | 0 | | |
| 3 | 6 | | | | | 4 | | |
| 4 | 0 | | | | | 1 | | |
| 5 | 2 | | | | | 4 | | |
| 6 | 8 | 7 | 3 | | 9 | 1 | | |
| 7 | 9 | 5 | 0 | | | 0 | | |
| 8 | 8 | 0 | 0 | | | 0 | | |
| 9 | 9 | 8 | 2 | | | 0 | | |
| 10 | 9 | 0 | 0 | | | 1 | | |
| 11 | 0 | | | | | 1 | | |
| 12 | 0 | | | 9 | | 0 | | |
| 13 | 9 | 9 | 0 | | | 2 | | |
| 14 | 9 | 9 | 7 | | | 9 | 4 | 0 |
| 15 | 8 | 6 | 0 | | | 7 | 0 | 0 |
| 16 | 9 | 9 | 0 | | | 3 | | |

EXAMPLE 18

Preparation And Evaluation Of 6-[m-(Trifluoromethyl)benzyl]-4-pyrimidinyl-α,α,α-trifluoro-m-tolyl-ketone, O-Methyloxime (E)- and (Z)-

3-Triflluoromethylphenylacetonitrile (2.04 g, 11 mmol) is added to THF (100 ml) under nitrogen and the reaction is chilled to −65° C. t-Butyl lithium (1.7N, 13 ml, 22 mmol) is then added slowly and after a further 5 minutes 4-chloro-6-(3-trifluoromethylbenzyl pyrimidine (3.0 g, 11 mmol) in THF (50 ml) is slowly added. The reaction is stirred at −65° C. for 1 hour and then at room temperature for 18 hours before being poured into ethyl acetate and 10% hydrochloric acid. The product is extracted into ethyl acetate, is washed with 10% hydrochloric acid and the combined organic layers dried over sodium sulphate. The organic solution is filtered and concentrated under vacuum to give 4.8 g brown solid which is triturated with methylene chloride to give 4-(3-trifluorophenylacetonitrile)-6-(3-trifluoromethyl-benzyl) pyrimidine (1.8 g) as a yellow powder. The filtrate is chromatographed to obtain 0.45 g additional material. $^1$H NMR CDCl$_3$ 4.18 (2H,s) 5.25 (1H,s) 7.3 (1H,d) 7.44–7.67 (8H,m) 9.13 (1H,d).

4-(3-Trifluorophenylacetonitrile)-6-(3-trifluoromethylbenzyl)pyrimidine (3.28 g, 7.8 mmol) is added to toluene (250 ml), sodium hydroxide (3.1 g, 78.0 mmoles) in water (150 ml) and tetrabutyl ammonium chloride (0.21 g, 0.78 mmol). The reaction is stirred at room temperature for 18 h at which time tetrabutyl ammonium chloride (0.4 g, 1.44 mmol) is added and the reaction mixture is stirred for 24 hours at room temperature. The product is then extracted into ethyl acetate, washed with brine, dried over sodium sulphate, filtered and concentrated to give a brown liquid. The crude product is chromatographed to give 1.4 g of 6-[m-(Trifluoromethyl)benzyl]-4-pyrimidinyl alpha,alpha,alpha-trifluoro-m-tolyl ketone as a yellow oil. $^1$H NMR CDCl$_3$ 4.30 (2H, s) 7.50–8.42 (8H, m) 7.8 (1H, d) 9.32 (1H, d)

6-[m-(Trifluoromethyl)benzyl]-4-pyrimidinyl alpha,alpha,alpha-trifluoro-m-tolyl ketone (0.45 g, 1.1 mmol), ethanol (50 ml) and O-methylhydroxylamine hydrochloride (0.45 g, 5.3 mmol) are combined and refluxed for 6 hours. The solvent is removed under vacuum, the residue is taken up in ethyl acetate and is washed with water, brine, dried over magnesium sulfate and the solvent is removed under vacuum to yield 0.30 g yellow oil of the syn and anti isomers of the title compound. $^1$H NMR CDCl$_3$ 3.99, 4.06 (3H, s) 4.21, 4.27 (2H, s) 7.49–7.80 (9H, m) 9.10, 9.30 (1H, d)

The activity of this compound is measured as described above and the results are shown below:

| Example | TSM | | | SAW | | | |
|---|---|---|---|---|---|---|---|
| | 300 (ppm) | 100 (ppm) | 10 (ppm) | 1000 (ppm) | 300 (ppm) | 100 (ppm) | 10 (ppm) |
| 18 | 7 | 5 | 0 | | 0 | | |

EXAMPLE 19

Preparation Of 4-(α,α,α-Trifluoro-N-methyl-m-toluidino)-6-[(α,α,α-trifluorom-toly)oxy]pyrimidine 4,6-Dichloropyrimidine (1.55 g, 0.01 mol) and N-metyl-3-trifluoromethylaniline (2.0 g, 0.11 mol) are combined and heated to 126° C. under N$_2$ for 1.5 hours. The resulting oil is taken up in ethyl acetate, is washed with 10% sodium carbonate and dried over sodium sulphate. The organic phase is concentrated under reduced pressure to yield a yellow oil which is purified by column chromatography to give 4-chloro-6-(N-methyl-3-trifluoromethylanilino)-pyrimidine (1.78 g) as a white solid.

4-Chloro-6-(N-methyl-3-trifluoromethylanilino)-pyrimidine (0.30 g, 0.001 mol.) and sodium carbonate (0.28 g, 0.003 mol.) in DMF are stirred for 10 minutes. m-Trifluoro-methylphenol (0.16 g, 0.001 mol) is added and the mixture is heated to 60° C. for 12 hours. The mixture is then cooled and poured into water. The product is extracted into ethyl acetate, washed with 10% sodium hydroxide, 10% hydrochloric acid, and 5% potassium carbonate, dried over Na$_2$SO$_4$, filtered, and is concentrated under reduced pressure. 6-(N-methyl-3-trifluoromethylanilino)-4-(3-trifluoromethyl-phenoxy)pyrimidine (0.16 g) obtained by chromatography as a white solid. M.p. 118–119° C.

EXAMPLES 20–29

Preparation And Evaluation Of Substituted Pyrimidine Compounds

Using essentially the same procedures described in Example 19 hereinabove, the following compounds in which $X_1$ is $NR_{14}$, $X_2$ is O and $R_1$, $R_2$, $R_5$, $R_6$, $R_7$, $R_8$ and $R_{11}$ are all hydrogen are prepared.

| Example | $R_4$ | $R_3$ | $R_9$ | $R_{10}$ | $R_{15}$ | M.p (C) |
|---|---|---|---|---|---|---|
| 20 | H | $CF_3$ | F | $CF_3$ | Me | 119–120 |
| 21 | H | $CF_3$ | Cl | Cl | Me | 70–71 |
| 22 | H | $CF_3$ | Cl | $CF_3$ | Me | 101–102 |
| 23 | F | $CF_3$ | H | $CF_3$ | Me | |
| 24 | F | $CF_3$ | Cl | $CF_3$ | Me | |
| 25 | Cl | $CF_3$ | F | $CF_3$ | Me | |
| 26 | Cl | Cl | H | $CF_3$ | Me | |
| 27 | Cl | Cl | F | $CF_3$ | Me | |
| 28 | Cl | Cl | Cl | Cl | Me | |
| 29 | F | $CF_3$ | F | $CF_3$ | Me | |

NMR characteristics of these compounds are shown below:
Example 23: $CDCl_3$: $^1$H NMR: 8.36 (1H,s), 7.64–7.28(7H, m), 5.87(1H,s),3.48(3H,s)
Example 24: $CDCl_3$: $^1$H NMR: 8.34(1H,s), 7.50–7.00(6H, m), 5.90(1H,s), 3.49(3H,s)
Example 25: $CDCl_3$: $^1$H NMR: 8.34(1H,s), 7.64–7.19(6H, m), 5.97(1H,s), 3.50(3H,s)
Example 26: $CDCl_3$: $^1$H NMR: 8.36(1H,s), 7.52–7.12(6H, m), 5.95(1H,s), 3.46(3H,s)
Example 27: $CDCl_3$: $^1$H NMR: 8.34(1H,s), 7.54–7.15(6H, m), 5.98(1H,s), 3.48(3H,s)
Example 28: $CDCl_3$: $^1$H NMR: 8.35(1H,s), 7.53–6.95(6H, m), 5.94(1H,s), 3.46(3H,s)
Example 29: $CDCl_3$: $^1$H NMR: 3.49 (3H, s) 5.85 (1H,d) 7.20–7.75(6H,m) 8.35 (1H,d)
The activity of these compounds is shown below:

trifluoromethylbenzyl)-4-(3H)-pyrimidin-one as a white flocculant solid. Mp 119–124° C.

2-Thioethyl-6-(3-trifluoromethylbenzyl)-4-(3H)-pyrimidin-one (5.8 g, 18.5 mmol) is suspended in phosphorous oxychloride (40 ml). N,N-dimethylaniline (2.24 g, 18.5 mmol) is added and the reaction is stirred for 2 hours at room temperature. The unchanged phosphorous oxychloride is removed under vacuum and the resulting red liquid (6.3 g) is directly in the next step.

4-Chloro-2-thioethyl-6-(3-trifluoromethylbenzyl)-pyrimidine (4.0 g, 18.5 mmol) is dissolved in DMF (40 ml). 3-trifluoromethylphenol (3.6 g, 22.2 mmol) and potassium carbonate (3.02 g, 22.2 mmol) are added and the reaction is heated under nitrogen at 50° C. for 19 hours and 100° C. for 4 hours. The reaction is partitioned between ethyl acetate and water. The organic is washed with water, brine,dried over magnesium sulfate and concentrated to give a brown oil which is filtered through a silica plug (ethyl acetate eluent). Heptane (20 ml) is added to the resulting oil and it is allowed to stand at 5° C. overnight. The resulting yellow solid is filtered to give 4.0 g of the 2-thioethyl-4-(3-trifluoromethylbenzyl)-6-(3-trifluoromethyl-phenoxy)-pyrimidine. $^1$H NMR $CDCl_3$ 1.14 (3H, t) 2.83 (2H,q) 4.06 (2H, s) 6.34 (1H, s) 7.3–7.6 (8H, m)

2-Thioethyl-4-(3-trifluoromethylbenzyl)-6-(3-trifluoromethylphenoxy)-pyrimidine (4.0 g, 8.7 mmol) is dissolved in methylene chloride (50 ml). m-chloroper-benzoic acid (60%, 5.0 g, 17.5 mmol) is added portionwise over 2 minutes and the reaction is stirred for one hour at room temperature. The solvent is removed under vacuum and the residue is taken up in ethyl acetate and is washed with 5% sodium metabisulfite, saturated sodium bicarbonate, brine and dried over magnesium sulfate. The solvent is removed

| | TSM | | | | SAW | | | | WCR |
|---|---|---|---|---|---|---|---|---|---|
| Example | 300 (ppm) | 100 (ppm) | 10 (ppm) | 1 (ppm) | 1000 (ppm) | 300 (ppm) | 100 (ppm) | 10 (ppm) | 50 (ppm) |
| 19 | 0 | | | | | 0 | | | 2 |
| 20 | 0 | | | | | 6 | 3 | 1 | |
| 21 | 9 | 0 | 0 | | | 0 | 0 | | |
| 22 | 0 | | | | | 3 | | | |
| 23 | 9 | 9 | 5 | 0 | | 9 | 7 | 0 | |
| 24 | 9 | 9 | 9 | 0 | | 9 | 4 | 0 | |
| 25 | 9 | 9 | 9 | 0 | | 4 | 5 | 0 | |
| 26 | 9 | | | | 9 | | | | |
| 27 | 9 | | | | 9 | | | | |
| 28 | 1 | | | | 3 | | | | |
| 29 | 9 | 9 | 9 | 6 | 9 | 9 | 9 | 1 | |

EXAMPLE 30

Preparation Of 4-[m-(Trifluoromethyl)benzyl]-6-[(α,α,α-trifluoro-m-tolyl)oxy]pyrimidine Ethyl-(3-trifluoromethylphenyl)acetoacetate (15.8 g, 57.6 mmol) is combined with ethanol (60 ml), water (60 ml) and 2-ethyl-2-thiopseudourea hydrobromide (12.8 g, 69.1 mmol). Potassium carbonate (9.5 g, 69.1 mmol) is added portionwise at room temperature over 1 minute under nitrogen and the reaction is stirred 18 hours. The reaction is added to 200 ml water and acetic acid (4.2 g, 69.1 mmol) and stirred for 5 minutes. The resulting white precipitate is filtered, taken up in ethyl acetate, washed with water, brine, and dried over magnesium sulfate. The solvent is removed under vacuum and the resulting solid is triturated with 240 ml heptane to afford 10.1 g of 2-thioethyl-6-(3- under vacuum to give 4.0 g of oil which is chromatographed yielding 2.8 g 2-(ethylsulfonyl)-4-[m-(trifluoromethyl)benzyl]-6-[(α,α,α-trifluoro-m-tolyl)oxy]pyrimidine as a clear viscous oil. $^1$H NMR $CDCl_3$ 1.27 (3H, t) 3.32 (2H,q) 4.29 (2H, s) 6.81 1H, s) 7.3–7.6 (8H)

2-(Ethylsulfonyl)-4-[m-(trifluoromethyl)benzyl] -6-[(α,α,α-trifluoro-m-tolyl)oxy]pyrimidine (1.17 g, 2.4 mmol) is added to chloroform (10 ml) and ethanol (10 ml). sodium borohydride (0.3 g, 7.9 mmol) is added portionwise over 15 minutes and the reaction is stirred at room temperature for 80 mins. The mixture is taken up in ethyl acetate and is washed with water, brine and dried over magnesium sulfate. The solvent is evaporated to give 1.05 g of a cloudy oil which is chromatographed to yield 0.89 g 4-[m-(trifluoromethyl)benzyl]-6-[(α,α,α-trifluoro-m-tolyl)oxy] pyrimidine as a water white oil. $^1$H NMR $CDCl_3$ 4.17 (2H, s) 6.75 (1H,s) 7.3–7.6 (8H, m) 8.71 (1H, s)

EXAMPLE 31

Preparation Of 2-(Dimethylamino)-4-[m-(trifluoromethyl)benzyl]-6-[(alpha,alpha,alpha-trifluoro-m-tolyl)oxy]pyrimidine 2-(Ethylsulfonyl)-4-[m-(trifluoromethyl)benzyl]-6-[(α,α,α-trifluoro-m-tolyl)oxy]pyrimidine (0.40 g, 0.82 mmol) is added to THF (20 ml). Dimethylamine hydrochloride (0.11 g, 13.4 mmol) and triethylamine (0.17 g, 16.8 mmol) is added and the reaction stirred at room temperature for 18 days. Ethyl acetate is added to the reaction and the organic phase is washed with water, brine and dried over magnesium sulfate. The solvent is removed under vacuum and the residue is chromatographed to afford 0.40 g 2-(Dimethylamino)-4-[m-(trifluoromethyl)-benzyl]-6-[(α,α,α-trifluoro-m-tolyl)oxy]pyrimidine as a yellow oil. $^1$H NMR CDCl$_3$ 3.02 (6H, b) 3.92 (2H, s) 5.87 (1H, s) 7.3–7.65 (8H, m).

EXAMPLE 32

Preparation Of 4-[(α,α-Dimethyl-m-(trifluoromethyl)benzyl]-6-[(α,α,α,4-tetrafluoro-m-tolyl)oxy]pyrimidine (3-Trifluoromethyl phenyl)acetic acid methyl ester (30 g, 0.138 mol), is added to THF (200 ml) under nitrogen. The reaction is cooled to −70° C. and (35.3 g, 0.315 mol) potassium tert-butoxide in THF (300 ml) is added slowly. The reaction is stirred at −70° C. for 10 minutes and methyl iodide (44.7 g, 0.315 mol) is added slowly. The reaction is stirred for 3 hours while allowing the temperature to rise to −30° C. and further stirred at room temperature for 18 h. The reaction is quenched with 10% hydrochloric acid and the product extracted into ethyl acetate. The organic phase is washed with water, saturated sodium meta bisulfite and dried over magnesium sulfate. The solvent is removed under vacuum to yield 29.1 g α,α-dimethyl-(3-trifluoromethylphenyl)acetic acid methyl ester as a yellow liquid. $^1$H NMR CDCl$_3$ 1.62 (6H, s) 3.67 (3H, s) 7.4–7.6 (4H,m)

α,α-Dimethyl-(3-trifluoromethylphenyl)acetic acid methyl ester (24.6 g, 0.1 mol), acetic acid (150 ml), water (75ml) and sulfuric acid (36 g, 0.36 mol) are combined. The reaction is refluxed for 3 hours and stirred at room temperature for 3 days. The reaction is concentrated to half its original volume and added to ethyl acetate and washed with water, dried over magnesium sulfate and concentrated under reduced pressure to give 16.6 g α,α-dimethyl-(3-trifluoromethylphenyl)acetic acid as a white solid. $^1$H NMR CDCl$_3$ 1.63 (6H,s) 7.45–7.65 (4H, m)

The α,α-dimethyl-(3-trifluoromethylphenyl)acetic acid is converted to 6-chloro 4-(α,α-dimethyl-3-trifluoromethylbenzyl)-pyrimidine as described above in Example 1.

6-Chloro4-(α,α-dimethyl-3-trifluoromethylbenzyl)-pyrimidine (10.45 g, 1.5 mmol), 4-fluoro-3-trifluoromethylphenol (0.30 g, 1.65 mmol) and potassium carbonate (0.30 g, 2.2 mmol) are combined in 15 ml of dimethyl formamide and heated to 70° C. for 18 hours. The reaction mixture is added to ethyl acetate, washed with water, 2.5% sodium hydroxide, brine and dried over magnesium sulfate. The solvent is removed under vacuum to afford 1.02 g of a brown oil which is chromatographed to afford 0.93 g of the title compound as a yellow oil. $^1$H NMR CDCl$_3$ 1.79 (6H, s) 6.78 (1H, d) 7.2–7.6 (7H, m) 8.71 (1H, d)

EXAMPLES 33–39

Preparation Of Substituted Pyrimidine Compounds

Using essentially the same procedure described hereinabove for Example 32 and employing the appropriate starting materials and reagents, the following compounds in which $X_1$ is $CR_{18}R_{19}$, $X_2$ is O and $R_1$, $R_2$, $R_5$, $R_6$, $R_7$, $R_8$ and $R_{11}$ are all hydrogen are prepared.

| Example | $R_{18}$ | $R_{19}$ | $R_4$ | $R_3$ | $R_9$ | $R_{10}$ |
|---|---|---|---|---|---|---|
| 33 | H | H | H | CF$_3$ | H | CF$_3$ |
| 34 | Methyl | Methyl | Cl | H | F | CF$_3$ |
| 35 | Methyl | Methyl | Cl | H | H | CF$_3$ |
| 36 | cyclopropyl | | Cl | H | H | CF$_3$ |
| 37 | cyclopropyl | | Cl | H | F | CF$_3$ |
| 38 | Methyl | Methyl | H | CF$_3$ | H | CF$_3$ |
| 39 | Methyl | Methyl | H | CF$_3$ | F | CF$_3$ |

The NMR characteristics of these compounds are shown below:

Example 33: CDCl$_3$: $^1$H NMR 4.17 (2H, s) 6.75 (1H,s) 7.3–7.6 (8H, m) 8.71 (1H, s)

Example 34: CDCl$_3$: $^1$H NMR 1.79 (6H, s) 6.82 (1H, d) 7.2–7.6 (7H,m) 8.71 (1H, d)

Example 35: CDCl$_3$: $^1$H NMR 1.74 (6H, s) 6.78 (1H, d) 7.2–7.6(8H,m) 8.71 (1H, d)

Example 36: CDCl$_3$: $^1$H NMR 1.37 (2H, m) 1.81 (2H, m)6.35 (1H, d) 7.3–7.5 (8H, m) 8.61 (1H, d)

Example 37: CDCl$_3$: $^1$H NMR 1.38 (2H, m) 1.82 (2H, m)6.35 (1H, d) 7.2–7.4 (7H, m) 8.59 (1H, d)

Example 38: CDCl$_3$: $^1$H NMR 1.78 (6H, s) 6.79 (1H, d) 7.3–7.6 (8H,m) 8.71 (1H, d)

Example 39: CDCl$_3$: $^1$H NMR 1.74 (6H, s) 6.78 (1H, d) 7.2–7.4 (7H, m) 8.70 (1H, d)

EXAMPLE 40

Insecticidal And Acaricidal Evaluation of Test Compounds

The activity of these compounds is shown below:

| Example | TSM twospotted mite | | | SAW southern army worm | | | |
|---|---|---|---|---|---|---|---|
| | 300 (ppm) | 100 (ppm) | 10 (ppm) | 3000 (ppm) | 1000 (ppm) | 300 (ppm) | 100 (ppm) |
| 23 | 9 | 9 | 0 | | | 1 | |
| 34 | 8 | 7 | 0 | | | 9 | 0 |
| 35 | 9 | 7 | 0 | | | 4 | |
| 36 | 9 | 6 | 0 | | | 0 | |
| 37 | 0 | | | | 9 | 0 | |
| 38 | 9 | 0 | 0 | | | 0 | |
| 39 | 0 | | | | | 8 | |

EXAMPLE 41

Preparation And Evaluation of 6-[(α,α,α,4-Tetrafluoro-m-tolyl)oxy]-4-pyrimidinyl α,α,α,-trifluoro-m-tolyl ketone 4-chloro-6-(3-trifluoromethylbenzyl) pyrimidine (0.30 g, 1.1 mmol), 4-fluoro-3-trifluoromethylphenol (0.24 g, 1.3 mmol) and potassium carbonate (0.19 g, 1.4 mmol) are combined in DMF (10 ml) and heated at 70° C. under a drying tube. The reaction is poured into ethyl acetate (50ml), washed with water, 2.5% sodium hydroxide, brine and dried over magnesium sulfate. The solvent is removed under vacuum and the residue chromatographed to obtain 0.1 g of the title compound as a yellow oil. $^1$H NMR CDCl$_3$ 7.63 (1H, d) 7.2–8.4 (7H, m) 8.90 (1H, d).

The activity of this compound is measured as described above and the results obtained are shown below:

| Ex-ample | TSM two spotted mite | | | SAW southern army worm | | | |
|---|---|---|---|---|---|---|---|
| | 300 (ppm) | 100 (ppm) | 10 (ppm) | 1000 (ppm) | 300 (ppm) | 100 (ppm) | 10 (ppm) |
| 41 | 9 | 8 | 5 | | | 0 | |

What is claimed is:
1. A compound of Formula I

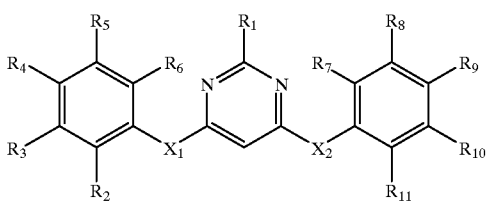

I wherein $R_1$ is hydrogen, $(C_{1-6})$alkylthio, halo$(C_{1-6})$alkylthio $(C_{1-6})$alkylsulphinyl, halo$(C_{1-6})$alkylsulphinyl, $(C_{1-6})$alkylsulphonyl, halo$(C_{1-6})$alkylsulphonyl or $NR_{12}R_{13}$;

$R_{12}$ and $R_{13}$ are each independently hydrogen,$(C_{1-6})$alkyl, or halo$(C_{1-6})$alkyl;

$R_2$, $R_3$, $R_4$, $R_5$, $R_6$, $R_7$, $R_8$, $R_9$ and $R_{11}$ are each independently selected from hydrogen, halogen, cyano, nitro, $(C_{1-6})$alkyl, halo$(C_{1-6})$alkyl, $(C_{1-6})$alkoxy, halo$(C_{1-6})$alkoxy, $(C_{1-6})$alkoxy$(C_{1-6})$alkyl, halo$(C_{1-6})$alkoxy$(C_{1-6})$alkyl, $(C_{1-6})$alkylthio, halo$(C_{1-6})$alkylthio, $(C_{1-6})$alkyl sulphinyl, halo$(C_{1-6})$alkylsulphinyl, $(C_{1-6})$alkylsulphonyl, halo$(C_{1-6})$alkylsulphonyl, amino, $(C_{1-6})$alkylamino, di$(C_{1-6})$alkylamino, halo$(C_{1-6})$alkylamino,$(C_{1-6})$alkylhaloalkyl$(C_{1-6}$amino, dihalo$(C_{1-6})$alkylamino, $(C_{1-6})$alkyloxy-carbonyl, halo$(C_{1-6})$alkyloxycarbonyl, $(C_{2-6})$alkenyl, halo$(C_{2-6})$alkenyl, $(C_{2-6})$alkynyl, halo$(C_{2-6})$alkynyl;

$R_{10}$ is halogen, halo$(C_{1-6})$alkyl, halo$(C_{2-6})$alkenyl or halo $(C_{2-6})$alkynyl;

and $X_1$ and $X_2$ are independently selected from the group consisting of $NR_{14}$, $NR_{15}$, O, $CH_2$, $CR_{18}R_{19}$, CO, $C=NOR_{20}$;

wherein $R_{14}$ is $(C_{1-6})$alkyl;

$R_{15}$ is H, $(C_{1-6})$alkyl or $CH(OR_{16})(OR_{17})$;

$R_{16}$ and $R_{17}$ are each independently $(C_{1-6})$alkyl;

$R_{18}$ and $R_{19}$ each independently selected from H, $(C_{1-6})$alkyl, $(C_{2-6})$alkenyl and $(C_{2-6})$alkynyl which are all optionally substituted by one or more halogens which are the same or different, or $R_{18}$ and $R_{19}$ may together form a carbocyclic ring which is optionally substituted by one or more halogens which are the same or different;

$R_{20}$ is $(C_{1-6})$alkyl;

with the proviso that $X_1$ cannot be the same as $X_2$, and with the proviso that the compound of formula 1 is not 4-[m-(trifluoromethyl)benzyl]-]6-(α,α,α-trifluoro-N-methyl-m-toluidino)pyrimidine.

2. The compound according to claim 1 wherein
a) one of $X_1$ and $X_2$ is $NR_{14}$ and the other is O;
b) one of $X_1$ and $X_2$ is $NR_{15}$ and the other is $CH_2$;
c) one of $X_1$ and $X_2$ is $CR_{18}R_{19}$ or CO and the other is O; or
d) one of $X_1$ and $X_2$ is $C=NOR_{20}$ and the other is $CH_2$.

3. The compound according to claim 1 wherein $X_1$ is $NR_{14}$ and $X_2$ is O.

4. The compound according to claim 1 wherein $X_1$ is $CH_2$ and $X_2$ is $NR_{15}$.

5. The compound according to claim 1 wherein $X_1$ is $CR_{18}R_{19}$ or CO and $X_2$ is O.

6. The compound according to claim 1 wherein $X_1$ is $C=NOR_{2O}$ and $X_2$ is $CH_2$.

7. The compound according to claim 1 wherein $R_{10}$ is chlorine, halo$(C_{1-4})$alkyl or halovinyl.

8. The compound according to claim 1 wherein $R_3$ is halogen, halo$(C_{1-6})$alkyl, halo$(C_{2-6})$alkenyl or halo$(C_{2-6})$alkynyl.

9. The compound according to claim 1 wherein $R_1$ is $(C_{1-6})$alkylthio, halo$(C_{1-6})$ alkylthio $(C_{1-6})$alkylsulfinyl, halo $(C_{1-6})$alkylsulfinyl, $(C_{1-6})$alkylsulfoxyl, halo$(C_{1-6})$alkylsulfoxyl or $NR_{12}R_{13}$; and one of $X_1$ and $X_2$ is $NR_{14}$ and the other is O.

10. A method for the control of acarina or insects which comprises contacting said acarid or insect or their habitats, breeding grounds or locus with a acaricidally or insecticidally effective amount of a compound described in claim 1.

11. A composition which comprises an agriculturally acceptable carrier and an acaricidally or insecticidally effective amount of a compound described in claim 1.

12. The compound according to claim 3 selected from the group consisting of:

4-(α,α,α,4-Tetrafluoro-n-methyl-m-toluidino)-6-[(α,α,α,4-tetrafluoro-m-tolyl)oxy]pyrimidine;
4-(α,α,α,4-Trifluoro-N-methyl-m-toluidino)-6-[(α,α,α,-trifluoro-m-tolyl)oxy]pyrimidine;
4-[(α,α,α,4-Tetrafluoro-m-tolyl)oxy]-6-(α,α,α,-trifluoro-N-methyl-m-toluidino)pyrimidine;
4-(3,4-Dichlorophenoxy)-6-(α,α,α,-trifluoro-N-methyl-m-toluidino)pyrimidine;
4-[(4-Chloro-α,α,α,-trifluoro-m-tolyl)oxy]-6-(α,α,α, trifluoro-N-methyl-m-toluidino)pyrimidine;
4-(α,α,α,4-Tetrafluoro-N-methyl-m-toluidino)-6-[(α,α,α, trifluoro-m-tolyl)oxy]pyrimidine;
4-[(4-Chloro-α,α,α,-trifluoro-m-tolyl)oxy]-6-(α,α,α,4-tetrafluoro-N-methyl-m-toluidino)pyrimidine;
4-(4-Chloro-α,α,α,-trifluoro-N-methyl-m-toluidino)-6-[(α, α,α,4-tetrafluoro-m-tolyl)oxy]pyrimidine;
4-(3,4-Dichloro-N-methylanilino)-6-[(α,α,α,-trifluoro-m-tolyl)oxy]pyrimidine;
4-(3,4-Dichloro-N-methylanilino)-6-[(α,α,α,-4-tetrafluoro-m-tolyl)oxy]pyrimidine; and
4-(3,4-Dichloro-N-methylanilino)-6-(3,4-dichlorophenoxy) pyrimidine.

13. The compound according to claim 4 selected from the group consisting of:

4-(α,α,α,4-Tetrafluoro-m-toluidino)-6-[m-(trifluoromethyl) benzyl]-, hydrochloride;
4-(3,4-Dichlorobenzyl)-6-(α,α,α,4-tetrafluoro-m-toluidino) hydrochloride;
4-(4-Chloro-α,α,α,-trifluoro-m-toluidino)-6-[m-(trifluoromethyl)benzyl]-, hydrochloride;
4-[m-(Trifluoromethyl)benzyl]-6-(α,α,α,-trifluoro-m-toluidino)pyrimidine, hydrochloride;
4-(α,α,α,4-Tetrafluoro-N-methyl-m-toluidino)-6-[m-trifluoromethyl)benzyl]pyrimidine;

4-(4-Chloro-α,α,α,-trifluoro-N-methyl-m-toluidino)-6-(3, 4-dichlorobenzyl)pyrimidine;

4-(3,4-Dichlorobenzyl)-6-(α,α,α,4-tetrafluoro-N-methyl-m-toluidino)pyrimidine;

4-(4-Chloro-α,α,α,-trifluoro-m-toluidino)-6-(3,4-dichlorobenzyl)pyrimidine;

4-(3,4-Dichlorobenzyl)-6-[N-diethoxymethyl)-α,α,α,4-tetrafuoro-m-toluidino]pyrimidine, 4-(4-Chloro-α,α,α,-trifluoro-N-methyl-m-toluidino)-6-[m-(trifluoromethyl)benzyl]pyrimidine;

4-(3,4-Dichlorobenzyl)-6-(α,α,α,-trifluoro-m-toluidino)pyrimidine;

4-(3,4-Dichlorobenzyl)-6-(α,α,α,-trifluoro-N-methyl-m-toluidino)pyrimidine;

6-(α,α,α,4-Tetrafluoro-m-toluidino)-4-[4-fluoro-3-(trifluoromethyl)benzyl]pyrimidine;

4-[4-Fluoro-3-(trifluolomethyl)benzyl]-6-(α,α,α,4-tetrafluoro-N-methyl-m-toluidino)pyrimidine, 4-(4-Chloro-α,α,α,-trifluoro-m-toluidino)-6-[4-fluoro-3-(trifluoromethyl)benzyl]pyrimidine; and 4-(4-Chloro-α,α,α,-trifluoro-N-methyl-m-toluidino)-6-[4-fluoro-3-trifluoromethyl)benzyl]pyrimidine.

14. The compound according to claim 5 selected from the group consisting of:

4-[m-(Trifluoromethyl)benzyl]-6-[(α,α,α,-trifluoro-m-tolyl)oxy]pyrimidine;

4-(p-Chloro-α,α,-dimethylbenzyl)-6-[(α,α,α,4-tetrafluoro-m-tolyl)oxy]pyrimidine;

4-(p-Chloro-α,α,-dimethylbenzyl)-6-[(α,α,α,4-trifluoro-m-tolyl)oxy]pyrimidine;

4-[1-(p-Chlorophenyl)cyclopropyl]-6-[(α,α,α,-trifluoro-m-tolyl)oxy]pyrimidine;

4-[1-(p-Chlorophenyl)cyclopropyl]-6-[(α,α,α,4-tetrafluoro-m-tolyl)oxy]pyrimidine, Ketone, 6-[(α,α,α,4-tetrafluoro-m-tolyl)oxy]4pyrimidinyl α,α,α,4-trifluoro-m-tolyl;

4-[α,α,-Dimethyl-m-(trifluoromethyl)benzyl]-6-[(α,α,α,-trifluoro-m-tolyl)oxy]pyrimidine; and 4-[α,α,-Dimethyl-m-(trifluoromethyl)benzyl]-6-[(α,α,α,4-tetrafluoro-m-tolyl)oxy]pyrimidine.

15. The compound according to claim 6 which is 6-[m-(Trifluoromethyl)benzyl]-4-pyrimidinyl α,α,α,-trifluoro-m-tolyl ketone, O-methyloxime, (E)- and (Z)-.

16. A process for the preparation of a compound of formula I wherein $X_1$, $X_2$, $R_1$, $R_2$, $R_3$, $R_4$, $R_5$, $R_6$, $R_7$, $R_8$, $R_9$, $R_{10}$ and $R_{11}$ are as described in claim 1 which comprises the following steps:

i) reacting a compound of formula IV

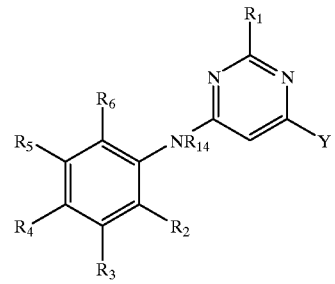

IV wherein Y is a halogen with a phenol of formula V

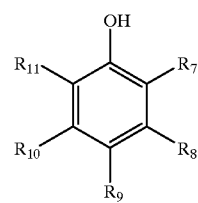

V to provide a compound of formula I wherein $X_1$ is $NR_{14}$ and $X_2$ is O.

* * * * *